United States Patent
Kolomeyer et al.

(10) Patent No.: US 6,884,913 B2
(45) Date of Patent: Apr. 26, 2005

(54) METHOD FOR PREPARATION OF ALPHA, BETA-UNSATURATED CYCLIC KETONES BY DEHYDROGENATION OF SECONDARY ALLYLIC CYCLIC ALCOHOLS

(75) Inventors: Gennadiy G. Kolomeyer, Jacksonville, FL (US); Jacob S. Oyloe, Jacksonville, FL (US)

(73) Assignee: Millennium Specialty Chemicals, Jacksonville, FL (US)

( * ) Notice: Subject to any disclaimer, the term of this patent is extended or adjusted under 35 U.S.C. 154(b) by 0 days.

(21) Appl. No.: 10/449,859

(22) Filed: May 30, 2003

(65) Prior Publication Data

US 2004/0215039 A1 Oct. 28, 2004

Related U.S. Application Data

(62) Division of application No. 09/824,234, filed on Apr. 3, 2001, now Pat. No. 6,610,873.

(51) Int. Cl.$^7$ ............................................. C07C 45/00
(52) U.S. Cl. ...................... 568/341; 568/361; 568/365
(58) Field of Search ................................. 568/341, 361, 568/365

(56) References Cited

U.S. PATENT DOCUMENTS

| | | | | |
|---|---|---|---|---|
| 2,918,495 A | * | 12/1959 | Booth | 568/341 |
| 4,160,786 A | | 7/1979 | Ehmann | 260/586 |
| 4,181,683 A | * | 1/1980 | Tsuji | 568/417 |
| 4,929,762 A | | 5/1990 | Matsunaga et al. | 568/361 |
| 5,241,122 A | | 8/1993 | Woell et al. | 568/485 |
| 5,817,891 A | | 10/1998 | Brücker et al. | 568/799 |
| 6,013,843 A | | 1/2000 | Aquila et al. | 568/473 |

FOREIGN PATENT DOCUMENTS

JP 50/58031 5/1975

OTHER PUBLICATIONS

Moody et al. Di–rhodium(II) carboxylate–catalysed oxidation of allylic and benzylic alcohols.☐☐Tetrahedron Letters, 2002 vol. 43 p 139–141.*
Blum et al. *Tetraedron Letters.* 21:1825–1828 (1970).
Fragale et al. *J Molecular Catalysis.* 5:65–73 (1979).
Hirata et al. *Phytochemistry.* 55(4):297–303 (2000).
Lempers et al. *J Org Chem.* 63:1408–1413 (1998).
Milos. Oxidations in Organic Chemistry, ACS Monograph 186. American Chemical Society, Washington, D.C., p. 114–115 (1990).
Ooi et al. *Synthesis.* 2:279–291 (2002).
Rothenberg. *J Chem Soc., Perkin Trans.* 2:2429–2434 (1998).
Sharpless et al. *Tetrahedron Letters.* 29:2503–2506 (1976).
Treibs et al. *Ber.* 60B:2335–2341 (1927).
Trost et al. *Israel Journal of Chemistry.* 24:134–143 (1984).
van der Drift et al. *J Organomet Chem.* 650:1–24 (2000).

* cited by examiner

*Primary Examiner*—Samuel Barts
*Assistant Examiner*—Sikarl A. Witherspoon
(74) *Attorney, Agent, or Firm*—Needle & Rosenberg, P.C.

(57) ABSTRACT

A process for the manufacture of an alpha, beta-unsaturated cyclic ketone, such as carvone, comprises the dehydrogenation of a secondary allylic cyclic alcohol, such as carveol, in the presence of at least one metal carboxylate. The process can be performed in a batchwise or continuous mode. Examples of suitable metal carboxylates include magnesium stearate, calcium 2-ethylhexanoate, and zinc 2-ethylhexanoate.

30 Claims, No Drawings

METHOD FOR PREPARATION OF ALPHA, BETA-UNSATURATED CYCLIC KETONES BY DEHYDROGENATION OF SECONDARY ALLYLIC CYCLIC ALCOHOLS

This application is a divisional of Ser. No. 09/824,234, filed on Apr. 3, 2001, and issued as U.S. Pat. No. 6,610,873.

material and the product possess double bonds, which can react with hydrogen that is produced as a result of dehydrogenation. Secondly, these double bonds easily isomerize at high temperature in the presence of catalysts to provide an aromatic structure. The scheme below represents these side reactions that can occur during, for example, the dehydrogenation of carveol.

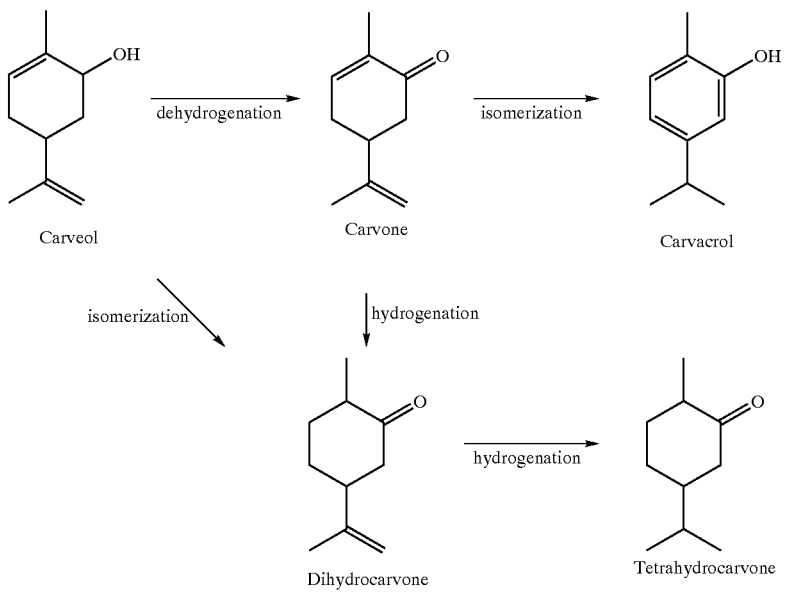

FIELD OF THE INVENTION

The present invention relates generally to the field of organic synthesis and more particularly to a process for the manufacture of an alpha, beta-unsaturated cyclic ketone, comprising the dehydrogenation of a secondary allylic alcohol in the presence of at least one metal carboxylate.

BACKGROUND OF THE INVENTION

It is known that many alcohols can be catalytically dehydrogenated to the corresponding carbonyl compounds (for general information see Hydlicky Milos, Oxidations in Organic Chemistry, ACS Monograph 186, American Chemical Society, Washington, D.C., 1990, p. 132 and Smith M. B. and March J. Advanced Organic Chemistry, $5^{th}$ edition, John Wiley and Sons, Inc., New York, 2001, pp. 1515–1516). Usually, dehydrogenation of alcohols allows preparation of the target carbonyl compounds with high yields and throughputs. To that end, copper, nickel, and palladium based catalysts have been typically used to carry out the dehydrogenation of alcohols.

An attempt to produce alpha, beta-unsaturated cyclic ketones, such as carvone, by catalytic dehydrogenation of a corresponding secondary allylic cyclic alcohol, such as carveol, was made in 1927 (Treibs W. and Schmidt H, Ber., 1927, 60 B, pp. 2335–2341). However, this attempt failed as both copper and nickel based catalysts converted the carveol into carvacrol and tetrahydrocarvone, but not to carvone. This was due, in part, to two potential side reactions that can accompany the catalytic dehydrogenation of a secondary allylic cyclic alcohol, such as carveol. First, both the starting Prior to the discovery of the present invention, most known methods for the preparation of alpha, beta-unsaturated cyclic ketones from a corresponding secondary allylic cyclic alcohol, such as the preparation of carvone from carveol, involve some type of an oxidation reaction. These methods can be divided in two categories.

The first of these two methods is known as the Oppenauer oxidation, where hydrogen is transferred from carveol to an auxiliary carbonyl compound. Japanese patent JP 50/58031 describes carveol oxidation in the presence of aluminum isopropoxide as catalyst, cyclohexanone as hydrogen acceptor, and xylene as solvent. The yield of the 88% pure carvone was 82%. A better yield of carvone (91%) was obtained by employing of a complex aluminum catalyst and three equivalents of pivalaldehyde as hydrogen acceptor in a methylene chloride solution (Takashi Ooi, et al, Synthesis, 2002, No. 2, pp. 279–291). The new aluminum complex catalyst used in this method (2,7-dimethyl-1,8-biphenyldioxy)bis(dialkoxyaluminum) has to be prepared from trialkylaluminum, which imposes safety concerns on an industrial scale. Common disadvantages of all Oppenauer type oxidation methods include the catalyst sensitivity toward hydrolysis, the necessity of use of an auxiliary carbonyl compound (sometimes a large excess) and a lengthy and labor intensive work-up.

The second of these methods is known as oxidation with a reagent. Above mentioned Japanese patent JP 50/58031 also describes carveol oxidation to carvone with chromic trioxide in concentrated sulfuric acid with 93% yield. Among other reagents suggested for carveol oxidation to carvone are, hydrogen peroxide in the presence of molybdenum catalyst (Trost, B. M. et al., Israel Journal of Chemistry, 1984, Vol. 24, pp. 134–143);

N-methylmorpholine-N-oxide in the presence of ruthenium catalyst (Sharpless K. B. et al., Tetrahedron Letters, 1976, No. 29, pp. 2503–2506); hydroperoxides in the presence of molybdenum and vanadium catalysts (Lempers H. E. B. et al., J. Org. Chem., 1998, Vol. 63, pp. 1408–1413); and copper catalysts (Rothenberg G., J. Chem. Soc., Perkin Trans. 1998, No. 2, pp. 2429–2434). In most, if not all, of these reactions expensive reagents or toxic catalysts are used and a large excess of the oxidation reagent is required, which makes a reagent oxidation very unattractive for commercialization.

The double bond in carvone that is conjugated with the carbonyl group is markedly active as hydrogen acceptor. This is why under commonly used dehydrogenation conditions dihydrocarvone becomes the major product of carveol dehydrogenation (see, for example, U.S. Pat. No. 4,160,786 which describes isomerization of cycloalkenols to cycloalkanones in the presence of copper-chromite catalysts and specifically mentions carveol conversion to dihydrocarvone). Supported palladium, platinum and ruthenium catalysts, which are frequently used in dehydrogenation reaction, afford phenols and cyclohexanones upon dehydrogenation of cycloalkenols (carveol) or cycloakenones (carvone). Examples of such transformations can be found in U.S. Pat. No. 4,929,762 and U.S. Pat. No. 5,817,891.

In some instances a method called oxidative dehydrogenation is employed to produce alpha,beta-unsaturated carbonyl compounds from the corresponding allylic alcohols. Catalysts utilized in this process include metallic copper or silver. Using this process geraniol was converted to citral (U.S. Pat. No. 5,241,122) and prenol to prenal (U.S. Pat. No. 6,013,843) at the temperature above 360° C. The name of this process—oxidative dehydrogenation—suggests that this is not a true dehydrogenation, as it requires the presence of oxygen, which could be either an oxidant or a hydrogen acceptor. Nonetheless, the oxidative dehydrogenation has never been successfully used to produce carvone, probably because it proceeds at the temperature above 360° C., which causes decomposition of carveol and carvone and leads to low yields and poor quality.

In other attempts, some enzymes have been found to affect this kind of chemical transformation (Hirata, T., et al., Phytochemistry, 2000, vol. 55, No. 4, pp. 297–303). The enzymatic method has mostly a theoretical interest and cannot be used for a large-scale production of carvone.

In general, homogeneous catalysts are rarely used in dehydrogenation process (Blum, J., Biger, S. Tetrahedron Letters, 1970, No. 21, pp. 1825–1828). In particular, in the presence of those homogeneous catalysts that could possibly affect dehydrogenation of the allylic alcohols the isomerization to saturated carbonyl compounds but not dehydrogenation to corresponding unsaturated carbonyl compounds was observed (see review by van der Drift, R. C. et al., J. Organomet. Chem., 2000, No. 650, pp. 1–24). There are a few examples of the homogeneous dehydrogenation of alcohols. However, only saturated alcohols were used as substrates (Fragale, C. et al. J. Molecular Catalysis, 1979, Vol. 5, pp. 65–73). Interestingly, most of the reported examples were not dehydrogenation, but rather hydrogen transfer reactions, which involved hydrogen acceptors. Thus, there is no indication in the patent or scientific literature that carvone or any other conjugated alpha, beta-unsaturated cyclic ketones can be prepared by catalytic dehydrogenation of the corresponding allylic alcohol.

Moreover, the homogeneous dehydrogenation catalysts that have been used are complex compounds of the transition metals chosen from groups six to ten of the Periodic Table. In contrast, the present invention further provides a method that utilizes carboxylates of the metals chosen from groups two and twelve of the Periodic Table. As discussed below, and in accordance with the present invention, these carboxylates are effective homogeneous dehydrogenation catalysts that allow for selective production of alpha, beta-unsaturated cyclic ketones from the corresponding secondary allylic cyclic alcohol via a true dehydrogenation mechanism.

SUMMARY OF THE INVENTION

Among other aspects, the present invention is based in part on the surprising discovery that carboxylates of metals from groups two and twelve of the Periodic Table can act as selective homogeneous catalysts for the dehydrogenation of a secondary allylic cyclic alcohol to form an alpha, beta-unsaturated cyclic ketone.

In a first aspect, the present invention provides a process for the manufacture of an alpha, beta-unsaturated cyclic ketone, comprising the dehydrogenation of a secondary allylic cyclic alcohol in the presence of at least one metal carboxylate, in a reaction environment under conditions effective to provide an alpha, beta-unsaturated cyclic ketone.

In a second aspect, the present invention further provides alpha, beta-unsaturated cyclic ketones produced by the processes described herein.

Additional advantages and embodiments of the invention will be obvious from the description, or may be learned by practice of the invention. Further advantages of the invention will also be realized and attained by means of the elements and combinations particularly pointed out in the appended claims. Thus, it is to be understood that both the foregoing general description and the following detailed description are exemplary and explanatory of certain embodiments of the invention, and are therefore not restrictive of the invention as claimed.

DETAILED DESCRIPTION OF THE INVENTION

The present invention may be understood more readily by reference to the following detailed description and any examples provided herein. It is also to be understood that this invention is not limited to the specific embodiments and methods described below, as specific components and/or reaction conditions may vary. Furthermore, the terminology used herein is used only for the purpose of describing particular embodiments of the present invention and is not intended to be limiting in any way.

It must also be noted that, as used in the specification and the appended claims, the singular forms "a," "an," and "the" comprise plural referents unless the context clearly dictates otherwise. For example, reference to a component in the singular is intended to comprise a plurality of components.

Ranges may be expressed herein as from "about" or "approximately" one particular value and/or to "about" or "approximately" another particular value. When such a range is expressed, another embodiment comprises from the one particular value and/or to the other particular value. Similarly, when values are expressed as approximations, by use of the antecedent "about," it will be understood that the particular value forms another embodiment.

As used herein, Group II and XXII metals are intended to include those metals belonging to Groups II and XXII of the Periodic Table.

As used herein, the term "alkyl" refers to a paraffinic hydrocarbon group which may be derived from an alkane by dropping one hydrogen from the formula. Non-limiting examples include $C_1$–$C_{20}$ alkane derivatives such as methyl, ethyl, propyl, isopropyl, butyl, t-butyl, and isobutyl. To this end, it should be understood that an alkyl substituent suitable for use in the present invention can be a branched or straight chain alkyl substituent.

As used herein, the term "alkenyl" is intended to refer to a substituent derived from the class of unsaturated hydrocarbons having one or more double bonds. Those containing only one double bond are referred to as alkenes or alkenyl substituents. Those with two or more double bonds are called alkadienes (alkadienyl), alkatrienes (alkatrienyl) and so on. Non-limiting examples include ethylene, propylene, butylene and the like. To this end, it should be understood that an alkenyl substituent suitable for use in the present invention can be substituted or unsubstituted.

As used herein, the term "aryl" refers to a compound or substituent whose molecules have the ring structure characteristic of benzene, naphthalene, phenanthrene, anthracene, and the like. That is to say, an aryl group typically contains either the 6-carbon ring of benzene or the condensed 6 carbon rings of other aromatic derivatives. For example, an aryl group can be a phenyl or naphthyl group. To this end, it should be understood that aryl substituents suitable for use with the present invention can be substituted or unsubstituted.

As used here, alpha, beta-unsaturated cyclic ketone refers to cyclic ketones having the following structure:

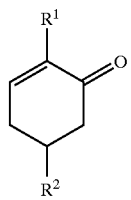

wherein $R^1$ and $R^2$ are independently selected from among straight chain or branched $C_1$–$C_5$ alkyl groups, $C_1$–$C_5$ alkenyl groups, or $C_6$–$C_{10}$ aryl groups.

As used herein, secondary allylic cyclic alcohol refers to an allylic cyclic alcohol having the following generic structure:

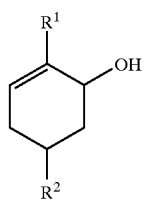

wherein $R^1$ and $R^2$ are independently selected from among straight chain or branched $C_1$–$C_5$ alkyl groups, $C_1$–$C_5$ alkenyl groups, or $C_6$–$C_{10}$ aryl groups.

As used herein, a beta, gamma-unsaturated cyclic ketone refers to a cyclic ketone having the following general structure:

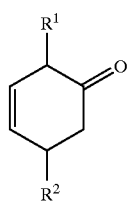

wherein $R^1$ and $R^2$ are independently selected from among straight chain or branched $C_1$–$C_5$ alkyl groups, $C_1$–$C_5$ alkenyl groups, or $C_6$–$C_{10}$ aryl groups.

As used herein, by use of the term "effective," "effective amount," or "conditions effective to" it is meant that such amount or reaction condition is capable of performing the function of the compound or property for which an effective amount is expressed. As will be pointed out below, the exact amount required will vary from one embodiment to another, depending on recognized variables such as the compounds or materials employed and the processing conditions observed. Thus, it is not always possible to specify an exact "effective amount" or "condition effective to." However, it should be understood that an appropriate effective amount will be readily determined by one of ordinary skill in the art using only routine experimentation.

As used herein, the term "reaction environment" refers to the medium in which the dehydrogenation reaction takes place. For example, and without limitation, the reaction environment or reaction medium in which the dehydrogenation reaction of the present invention takes place can be a secondary allylic cyclic alcohol. Alternatively, the reaction environment or reaction medium can comprise at least one optional solvent.

As used herein, the term "optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyl where there is substitution.

As set forth above, in a first aspect the present invention provides a process for the manufacture of an alpha, beta-unsaturated cyclic ketone, comprising the dehydrogenation of a secondary allylic cyclic alcohol in the presence of at least one metal carboxylate, in a reaction environment under conditions effective to provide an alpha, beta-unsaturated cyclic ketone.

According to the invention, suitable secondary allylic cyclic alcohols include those alcohols having the general structure of formula (I):

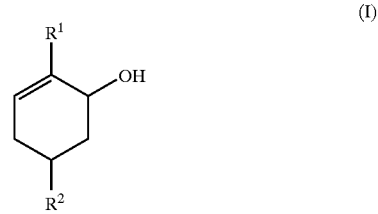

wherein $R^1$ and $R^2$ are independently selected from among straight chain or branched $C_1$–$C_5$ alkyl groups, $C_1$–$C_5$ alkenyl groups, or $C_6$–$C_{10}$ aryl groups. In a preferred aspect of the invention, the secondary allylic cyclic alcohol is carveol and is represented by the structure of formula (III) below:

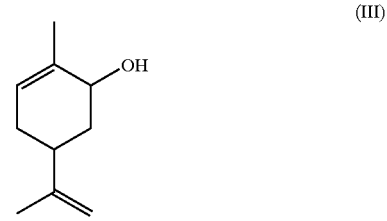

As stated above, the dehydrogenation process of the present invention proceeds in the presence of at least one metal carboxylate catalyst. The metal carboxylate catalysts are carboxylates of the metals selected from Groups II and XXII of the periodic table, including magnesium, calcium, and zinc. According to one aspect of the invention, the metal carboxylates comprise a carboxylate moiety having the general structure:

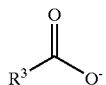

wherein $R^3$ is selected from among C1–C20 straight chain or branched alkyl groups, which groups can be further substituted by one or more additional C1–C20 straight chain or branched alkyl radicals. In one aspect, a preferred carboxylate is stearate. Alternatively, in another aspect, the carboxylate is an ethylhexanoate or octanoate. Therefore, in accordance with these aspects, suitable metal carboxylate catalyst for use in the present invention includes, without limitation, magnesium stearate (commercially available from the Aldrich company), calcium 2-ethylhexanoate (commercially available from Shepherd Chemical Company) and zinc 2-ethylhexanoate (also commercially available from Shepherd Chemical Company).

As described herein, the process of the present invention is useful for the manufacture of a variety of alpha, beta-unsaturated cyclic ketones having the generic structure:

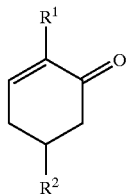

wherein $R^1$ and $R^2$ are independently selected from among straight chain or branched $C_1$–$C_5$ alkyl groups, $C_1$–$C_5$ alkenyl groups, or $C_6$–$C_{10}$ aryl groups. To that end, it will be understood and appreciated by one of ordinary skill in the art the particular alpha, beta-unsaturated cyclic ketone desired to be manufactured will be dependent upon the starting secondary allylic cyclic alcohol as previously described herein. In one aspect, the process of the present invention is particularly useful for the preparation of carvone, an alpha, beta-unsaturated cyclic ketone having the structure as follows.

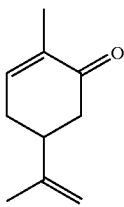

Using appropriate reaction conditions, not only allylic but also some other alcohols could be converted to the corresponding carbonyl compounds. For example, dihydrocarveol was converted to dihydrocarvone, although the rate of this reaction was slower, which indicates that allylic alcohols undergo metal carboxylate catalyzed dehydrogenation faster than their saturated analogues.

In the presence of metal carboxylates a noticeable rate of carveol dehydrogenation can be observed at about 210° C. However, to achieve a reasonable reaction rate the process should be carried out at 215–260° C. At higher temperature the selectivity of carveol dehydrogenation to carveol starts to decrease.

According to present invention, dehydrogenation of carveol is carried out in the presence of metal carboxylate at elevated temperature under atmospheric or reduced pressure as a batch or semi-continuous process with an optional addition of a solvent.

To this end, optimization of the process, as described herein, would be possible using only routine experimentation. For example, by controlling the residual pressure (e.g., vacuum), the reaction mixture can be refluxed at the desired temperature in the system. In addition, the choice of a desired temperature and residual pressure combination can control the carveol concentration in the system and, thus, the contact time between the catalyst and carveol. And, finally, this combination of parameters, e.g., pressure, carveol concentration, and contact time, can be used to select a feed rate of, e.g., carveol or carveol containing mixture to the system.

The reaction does not require a solvent, though addition of solvent can be beneficial in achieving high yields in a batch mode or for improving heat transfer and lowering the viscosity in a semi-continuous mode. Examples of solvents include but are not limited to high boiling individual hydrocarbons and their mixtures (pentadecane, white mineral oils, etc.), ethers (diphenyl ether, tetraethylene glycol dimethyl ether, etc.) or mixtures of hydrocarbons and ethers. The amount of solvent may vary from 10% to 200% based on starting carveol. Even larger amount of solvent can be employed. However, it would lead to less effective equipment utilization.

The process of the present invention as described herein can be successfully performed on virtually any scale.

The amount of catalyst can be expressed in terms of the starting secondary alcohol or the total reaction mixture. For example, the amount of the carboxylate can vary from about 0.5% by weight or less to about 100% by weight or more relative to the secondary alcohol. For example, specific examples of suitable amounts can include 1, 5, 10, 20, 30, 40, 50, 60, 70, 80 and 90% by weight and ranges therebetween.

Moreover, the amount of metal carboxylate catalyst is selected to provide the desired reaction rate and can vary depending on the reaction technique employed. For example, where the process is carried out in a batchwise mode, the carboxylate can be present in an amount of about 1% to about 4% by weight based on the starting secondary alcohol or about 0.5% to about 2 wt % based on the total reaction mixture. For processes carried out in the continuous mode, the metal carboxylate can be present in the system, based on throughput, of about 0.01 to about 1 g of secondary alcohol per 1 g of catalyst per hour.

To carry out a batch dehydrogenation carveol or carveol containing streams are mixed with catalyst and possibly a solvent in any sequence. Then the resulting mixture is heated at desired temperature. It is advisable, although not required, to remove any water contained in the optional solvent or in the feed by distillation (possibly adding an azeotrope forming agent) prior to catalyst addition in order to protect the catalyst from hydrolysis. Various hydrocarbons with appropriate boiling points can serve as azeotrope forming agents. Dehydrogenation can be carried out at reflux temperature, atmospheric pressure or under vacuum. The reflux temperature can be controlled by addition of one or more solvents or by adjusting pressure.

To carry out a semi-continuous process, a mixture of catalyst and solvent can be heated at the desired temperature (typically 220–250° C.) and pressure (typically 10–100 mm Hg) in the still pot of a distillation column efficient enough to separate carvone from carveol. Then carveol or containing stream is continuously added through the still-pot at a specified rate. As carvone has a lower boiling point, it is continuously removed from the top of distillation column, while carveol remains in the pot. Addition of carveol and removal of carvone are continued until the catalyst loses its activity (typically 96–120 hours). Semi-continuous process affords better yield of carvone comparing with batch process because the product is removed from the reaction zone as soon as it is formed thus preventing formation of by-products.

At high temperatures in the presence of catalyst, it is possible that the desired alpha, beta-unsaturated cyclic ketone will exists in equilibrium with its unconjugated isomer, a beta, gamma-unsaturated cyclic ketone, as illustrated below.

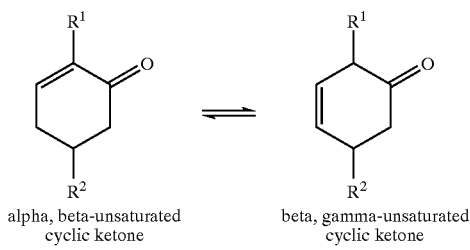

alpha, beta-unsaturated cyclic ketone     beta, gamma-unsaturated cyclic ketone

In instances where the unconjugated beta, gamma-unsaturated isomer has a lower boiling point than the target conjugated alpha, beta-unsaturated cyclic ketone, the beta, gamma-unsaturated cyclic ketone would be removed first during reflux conditions. For this reason, a product of a semi-continuous dehydrogenation of a suitable secondary allylic alcohol may contain a noticeable amount of the beta, gamma-unsaturated cyclic ketone in addition to the target alpha, beta-unsaturated cyclic ketone. For example, spicatone, the unconjugated beta, gamma-unsaturated isomer of carvone, has a lower boiling point than carvone and under reflux conditions is removed first. For this reason, a product of a semi-continuous dehydrogenation of carveol can contain a noticeable amount of spicatone, an amount typically in the range of from about 4 to about 8%.

A beta, gamma-unsaturated cyclic ketone, such as spicatone, can be isomerized back to the target alpha, beta-unsaturated cyclic ketone by heating the product of the dehydrogenation reaction to a temperature above 200° C. or by treating the product of the dehydrogenation reaction with a sodium hydroxide solution at or above 80° C. in a batch process. For example, according to the process of the present invention, the preparation of carvone from carveol can provide a minimum undesired amount of spicatone, the unconjugated alpha, gamma-unsaturated cyclic ketone isomer of carvone. By heating the product of dehydrogenation at above 200° C. or by treating with a sodium hydroxide solution at above 80° C. in a batch process, the spicatone can therefore be isomerized back to provide a higher yield of the desired product.

After the spicatone isomerization step, semi-continuous dehydrogenation of carveol affords 97% weight yield of 95% pure carvone (the rest 5% is mostly dihydrocarvone, which by itself is a valuable component of the spearmint oil). Further fractionation affords 99.6% pure (or higher) fragrance and flavor quality carvone with 90% yield based on starting carveol.

It will further be appreciated upon practicing the process of the present invention that the dehydrogenation process described herein does not alter the optical activity of starting secondary allylic cyclic alcohol. Therefore, a levorotatory secondary allylic cyclic alcohol, such as 1-carveol, can be successfully converted to a levorotatory alpha, beta-unsaturated cyclic ketone, such as 1-carvone. Likewise, the same holds true if the dextrorotatory alpha, beta-unsaturated cyclic ketone is the desired product. Thus, the present invention offers a convenient, practical, selective, relatively inexpensive and environmentally friendly process for the preparation of pure optical isomers of alpha, beta-unsaturated cyclic ketones, when they possess an asymmetric center.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.); however, some errors and deviations may have occurred. Unless indicated otherwise, parts are parts by weight, temperature is degrees C.

Example 1

A mixture of 30 g of 1-carveol and 0.6 g of zinc octoate (zinc content 18%, Shepherd Chemical Company) was heated at 228–230° C. in a flask equipped with a stirrer, temperature probe, and reflux condenser. Periodically the reaction mixture was sampled and analyzed by GC on a polar 30-meter capillary column. After 2 hours the reaction mixture contained 79% 1-carvone and 8% of unreacted 1-carveol (92% conversion of 1-carveol and 85.8% selectivity to 1-carvone).

Example 2

A mixture of 100 g 1-carveol, 3 g zinc octoate (zinc content 22%, Shepherd Chemical Company), 80 g dodecane was refluxed at 215–217° C. Water was removed using Dean-Stark trap. The reaction mixture was periodically sampled for GC analysis. After 10 hours the reaction mixture contained 79% carvone and 17% carveol (83% conversion, 95% selectivity).

Example 3

A mixture of 80 g 1-carveol, 2.5 g calcium octoate (calcium content 10%, Shepherd Chemical Company), 80 g tetraethylene glycol dimethyl ether, and 20 g cis-pinane was refluxed at 224–225° C. Water was removed using Dean-Stark trap. The reaction mixture was periodically sampled for GC analysis. After 5 hours the reaction mixture contained 28% carvone and 61% carveol (39% conversion, 71.8% selectivity).

Example 4

A mixture of 80 g carveol, 2.7 g magnesium stearate, 80 g tetraethylene glycol dimethyl ether, and 20 g cis-pinene was refluxed at 224–225° C. Water was removed using a Dean-Stark trap. The reaction mixture was periodically sampled for GC analysis. After 5 hours the reaction mixture contained 20% carvone and 69% carveol (31% conversion, 64.5% selectivity).

Example 5

A mixture of 80 g carveol, 3 g zinc octoate (zinc content 22%, Shepherd Chemical Company), 80 g diphenyl ether, and 16 g cis-pinene was refluxed at 224–225° C. Water was removed using a Dean-Stark trap. The reaction mixture was periodically sampled for GC analysis. After 6 hours the reaction mixture contained 82% carvone and 3% carveol (97% conversion, 84% selectivity).

Example 6

Semi-continuous dehydrogenation of 1-carveol. A mixture of 450 g mineral oil and 200 g zinc octoate (22% zinc) was heated in a 2-liter pot of a distillation column (25 theory plates) to 240° C. at 50 mm Hg. Then 7080 g of 1-carveol containing mixture (10.5% 1-carvone and 72.5% 1-carveol) was added through the pot at a rate of 60 g/h over 118 hours. The reflux ratio and the product take-off rate were adjusted in such a way so as to maintain pot temperature at 240–250° C. and the residual carveol content in the product (distillate) below 3.5%. Total 6800 g of product of dehydrogenation was collected. It contained 4.1% spicatone, 74.3% carvone, and 3.2% carveol (carveol conversion was 95.7%, and selectivity to carvone plus spicatone was 93%).

Isomerization of spicatone to carvone. The product of dehydrogenation was agitated at 100° C. for 2 hours with 25% (weight) of 10% aqueous solution of sodium hydroxide. The spicatone concentration decreased to 0.2% and carvone concentration increased to 78.2%. After the caustic solution was separated, the organic layer was neutralized with acetic acid and washed with water. Fragrance and flavor quality 99.6% pure 1-carvone was isolated using conventional methods of separation.

Isomerization of spicatone to carvone (alternative method). The product of dehydrogenation was agitated at 225° C. for 3 hours. The spicatone concentration decreased to 0.2% and carvone concentration increased to 78.1%. Fragrance and flavor quality 99.6% pure 1-carvone was isolated using conventional methods of separation.

Throughout this application, where various publications are referenced, the entire disclosures of these publications are hereby incorporated by reference into this application for all purposes.

While this invention has been described in connection with preferred embodiments and specific examples, it is not intended to limit the scope of the invention to the particular embodiments set forth, but on the contrary, it is intended to cover such alternatives, modifications, and equivalents as may be included within the spirit and scope of the invention as defined by the appended claims. For example, there are numerous variations and combinations of components and or conditions, e.g., the secondary allylic alcohol compound, the particular metal carboxylate, and the reaction conditions that can be used to optimize the results obtained from the described embodiments. To this end, one skilled in the art will appreciate that in practicing the present invention, only reasonable and routine experimentation will be required to optimize such conditions for the desired result.

What is claimed is:

1. A process for the manufacture of an alpha, beta-unsaturated cyclic ketone, comprising the dehydrogenation of a secondary allylic cyclic alcohol having the general structure:

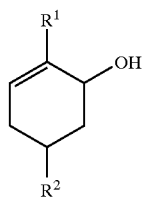

in the presence of at least one metal carboxylate, in a reaction environment under conditions effective to provide an alpha, beta-unsaturated cyclic ketone of the general structure:

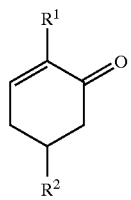

wherein $R^1$ and $R^2$ are independently selected from among straight chain or branched $C_1$–$C_5$ alkyl groups, $C_1$–$C_5$ alkenyl groups, or $C_6$–$C_{10}$ aryl groups.

2. The process of claim 1, wherein the secondary allylic cyclic alcohol is carveol and has the structure:

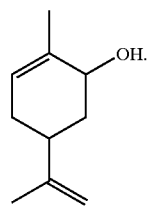

3. The process of claim 1, wherein the alpha, beta-unsaturated cyclic ketone is carvone and has the structure:

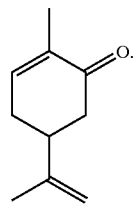

4. The process of claim 1, wherein the at least one metal is selected from Groups 2 and 12 of the periodic table.

5. The process of claim 1, wherein the at least one metal is magnesium, calcium, zinc, or any combination thereof.

6. The process of claim 1, wherein the at least one metal is zinc.

7. The process of claim 1, wherein the at least one metal carboxylate is magnesium stearate, calcium 2-ethylhexanoate, zinc 2-ethylhexanoate or any combination thereof.

8. The process of claim 1, wherein the at least one metal carboxylate is zinc 2-ethylhexanoate.

9. The process of claim 1, wherein the reaction environment comprises at least one solvent.

10. The process of claim 9, wherein the at least one solvent comprises an aliphatic hydrocarbon.

11. The process of claim 9, wherein the at least one solvent comprises an ether.

12. The process of claim 9, wherein the at least one solvent comprises cis-pinane, dodecane, pentadecane, mineral oil, diphenyl ether, tetraethylene glycol dimethyl ether or any combination thereof.

13. The process of claim 9, wherein the at least one solvent is present in an amount of from about from 0.5 wt. % to about 400 wt. % based on the secondary alcohol.

14. The process of claim 1, wherein the at least one metal carboxylate is present in an amount of from approximately 0.5% by weight to approximately 100% by weight relative to the secondary alcohol.

15. The process of claim 1, wherein the conditions effective to provide an alpha, beta-unsaturated cyclic ketone comprise heating the reaction environment.

16. The process of claim 15, wherein the reaction environment is heated to a temperature within the range of from approximately 210° C. to approximately 260° C.

17. The process of claim 1, wherein the conditions effective to provide an alpha, beta-unsaturated cyclic ketone comprise maintaining the reaction environment at or below atmospheric pressure.

18. The process of claim 1, wherein the condition effective to provide an alpha, beta-unsaturated cyclic ketone comprise refluxing the reaction environment.

19. The process of claim 1, wherein the process is carried out in a batchwise mode.

20. The process of claim 19, wherein the at least one metal carboxylate is present in an amount of 1–4 wt. % based on starting secondary alcohol.

21. The process of claim 19, wherein the at least one metal carboxylate is present in an amount of 0.5–2 wt. % based on total reaction mixture.

22. The process of claim 1, wherein the process is carried out in a continuous mode.

23. The process of claim 22, wherein the at least one metal carboxylate is present in the reaction environment, based on throughput, of 0.01–1 g of secondary alcohol per 1 g catalyst per hour.

24. The process of claim 22, wherein the alpha, beta-unsaturated cyclic ketone is continuously removed from the reaction environment.

25. The process of claim 1, wherein the process further comprises removing water from the reaction environment.

26. The process of claim 1, wherein the process further provides a beta, gamma-unsaturated cyclic ketone.

27. The process of claim 26, wherein the beta, gamma-unsaturated cyclic ketone is spicatone.

28. The process of claim 26, wherein the process further comprises an isomerization step to isomerize beta, gamma-unsaturated cyclic ketone to an alpha, beta-unsaturated cyclic ketone.

29. The process of claim 26, wherein the isomerization step is performed thermally by heating beta, gamma-unsaturated cyclic ketone to a temperature in the range of from approximately 200° C. to approximately 240°.

30. The process of claim 26, wherein the isomerization step is performed by treating beta, gamma-unsaturated cyclic ketone with a sodium hydroxide solution.

* * * * *